(12) United States Patent
Mo et al.

(10) Patent No.: US 6,997,876 B2
(45) Date of Patent: *Feb. 14, 2006

(54) ULTRASOUND CLUTTER FILTERING WITH ITERATIVE HIGH PASS FILTER SELECTION

(75) Inventors: Larry Y. L. Mo, San Ramon, CA (US); Ching-Hua Chou, Fremont, CA (US); Ting-Lan Ji, San Jose, CA (US); Glen W. McLaughlin, Saratoga, CA (US)

(73) Assignee: Zonare Medical Systems, Inc., Mountain View, CA (US)

( * ) Notice: Subject to any disclaimer, the term of this patent is extended or adjusted under 35 U.S.C. 154(b) by 83 days.

This patent is subject to a terminal disclaimer.

(21) Appl. No.: 10/825,719

(22) Filed: Apr. 16, 2004

(65) Prior Publication Data

US 2004/0199078 A1 Oct. 7, 2004

Related U.S. Application Data

(63) Continuation of application No. 10/167,606, filed on Jun. 11, 2002, now Pat. No. 6,733,455, which is a continuation-in-part of application No. 10/081,542, filed on Feb. 20, 2002, now abandoned, which is a continuation-in-part of application No. 09/860,209, filed on May 18, 2001, now Pat. No. 6,569,102, which is a continuation of application No. 09/378,175, filed on Aug. 20, 1999, now Pat. No. 6,251,073.

(60) Provisional application No. 60/370,632, filed on Apr. 5, 2002.

(51) Int. Cl.
 *A61B 8/06* (2006.01)
(52) U.S. Cl. .................................................. 600/455
(58) Field of Classification Search ........ 600/453–456; 73/861.25

See application file for complete search history.

(56) References Cited

U.S. PATENT DOCUMENTS

| | | | |
|---|---|---|---|
| 4,324,258 A * | 4/1982 | Huebscher et al. ......... 600/455 |
| 5,228,009 A | 7/1993 | Forestieri et al. |
| 5,269,308 A | 12/1993 | Hagiwara et al. |
| 5,295,485 A | 3/1994 | Shinomura et al. |
| 5,299,174 A | 3/1994 | Foirestieri et al. |
| 5,349,524 A | 9/1994 | Daft et al. |
| 5,349,525 A | 9/1994 | Dunki-Jacobs et al. |
| 5,383,464 A | 1/1995 | Shiba |
| 5,425,366 A | 6/1995 | Reinhardt et al. |

(Continued)

FOREIGN PATENT DOCUMENTS

EP 0 573 249 B1 4/1998

(Continued)

OTHER PUBLICATIONS

A. Pesavento et al., "Compression of Ultrasonic RF Data," IEEE Proc. Ultrasonics Symposium, 1997.

(Continued)

*Primary Examiner*—Francis J. Jaworski
(74) *Attorney, Agent, or Firm*—Carr & Ferrell LLP

(57) ABSTRACT

A system and method for ultrasound clutter filtering is provided. A processor is configured to iteratively select an optimal high pass filter for the progressive, ordered filtering of clutter from ultrasound color flow imaging data. The high pass filter input for each iterative selection and ordered set of high pass filters is the same original ultrasound color flow imaging data. The high pass filters have different cutoff frequencies whereby each high pass filter can be implemented using different structures. The system and method allow for filtering of clutter from ultrasound color flow imaging data until the clutter is substantially removed.

36 Claims, 10 Drawing Sheets

U.S. PATENT DOCUMENTS

| | | | |
|---|---|---|---|
| 5,442,940 A | 8/1995 | Secker et al. | |
| 5,443,071 A | 8/1995 | Banjanin et al. | |
| 5,445,156 A | 8/1995 | Daft et al. | |
| 5,476,010 A | 12/1995 | Fleming et al. | |
| 5,483,963 A | 1/1996 | Butler et al. | |
| 5,494,037 A | 2/1996 | Banjanin et al. | |
| 5,524,629 A | 6/1996 | Mahony | |
| 5,541,468 A | 7/1996 | Frey et al. | |
| 5,544,659 A | 8/1996 | Banjanin | |
| 5,559,301 A | 9/1996 | Bryan, Jr. et al. | |
| 5,590,658 A | 1/1997 | Chiang et al. | |
| 5,617,862 A | 4/1997 | Cole et al. | |
| 5,621,903 A | 4/1997 | Luciw et al. | |
| 5,633,912 A | 5/1997 | Tsoi | |
| 5,640,960 A | 6/1997 | Jones et al. | |
| 5,694,562 A | 12/1997 | Fisher | |
| 5,699,244 A | 12/1997 | Clark, Jr. et al. | |
| 5,714,971 A | 2/1998 | Shalit et al. | |
| 5,727,174 A | 3/1998 | Apraricio, IV et al. | |
| 5,738,099 A | 4/1998 | Chang | |
| 5,745,716 A | 4/1998 | Tchao et al. | |
| 5,748,927 A | 5/1998 | Stein et al. | |
| 5,749,072 A | 5/1998 | Mazurkiewicz et al. | |
| 5,754,179 A | 5/1998 | Hocker et al. | |
| 5,774,540 A | 6/1998 | Davidson et al. | |
| 5,782,769 A | 7/1998 | Hwang et al. | |
| 5,805,159 A | 9/1998 | Bertram et al. | |
| 5,839,442 A | 11/1998 | Chiang et al. | |
| 5,851,186 A | 12/1998 | Wood et al. | |
| 5,873,830 A | 2/1999 | Hossack et al. | |
| 5,901,246 A | 5/1999 | Hoffberg et al. | |
| 5,910,118 A | 6/1999 | Kanda et al. | |
| 5,919,138 A | 7/1999 | Ustuner | |
| 5,923,325 A | 7/1999 | Barber et al. | |
| 5,951,479 A | 9/1999 | Holm et al. | |
| 5,961,461 A * | 10/1999 | Mo et al. | 600/443 |
| 5,964,709 A | 10/1999 | Chiang et al. | |
| 5,997,478 A | 12/1999 | Jackson et al. | |
| 6,055,439 A | 4/2000 | Helin et al. | |
| 6,055,861 A | 5/2000 | Banta, Jr. et al. | |
| 6,063,030 A | 5/2000 | Vara et al. | |
| 6,117,079 A | 9/2000 | Brackett et al. | |
| 6,126,608 A | 10/2000 | Kemme et al. | |
| 6,135,960 A | 10/2000 | Holmberg | |
| 6,141,011 A | 10/2000 | Bodnar et al. | |
| 6,146,331 A | 11/2000 | Wong | |
| 6,210,334 B1 | 4/2001 | Phillips | |
| 6,230,043 B1 | 5/2001 | Johnson | |
| 6,251,073 B1 | 6/2001 | Imran et al. | |
| 6,287,258 B1 | 9/2001 | Phillips | |
| 6,296,612 B1 * | 10/2001 | Mo et al. | 600/455 |
| 6,309,357 B1 | 10/2001 | Guracar et al. | |
| 6,417,874 B2 | 7/2002 | Bodnar | |
| 6,569,102 B2 | 5/2003 | McLaughlin et al. | |
| 6,689,064 B2 * | 2/2004 | Hager et al. | 600/454 |
| 6,733,455 B2 * | 5/2004 | Mo et al. | 600/454 |
| 2001/0004260 A1 | 6/2001 | Bauer et al. | |
| 2002/0138002 A1 | 9/2002 | Tarakci et al. | |
| 2002/0188199 A1 | 12/2002 | Ji et al. | |

FOREIGN PATENT DOCUMENTS

EP  0 524 774 B1  5/1999

OTHER PUBLICATIONS

K. Rigby et al., "Real Time Adaptive Imaging," IEEE Ultrasonics Symposium, pp. 1603-1606, 1998.

C.M. Fabian et al, "Development of a Parallel Acquisition System of Ultrasound Research," IEEE Proc. Ultrasonics Symposium, 2001.

C.M. Fabian et al, "Development of a Parallel ACquisition System of Ultrasound Research," Department of Electrical Eng., University of Virginia (2001), pp. 1-9.

Vaitkus et al, "A Comparative Study and Assessment of Doppler Ultrasound Spectral Estimation Techniques Part 2," Ultrasound in Med. & Biol., vol. 14, No. 8, 1988, pp. 673-688.

Kay, "Modern Spectral Estimation: Theory and Application," Prentice Hall, 1988, pp. 217-237.

Clarkson, "Optimal and Adaptive Signal Processing," CRC Press, 1993, pp. 330-340.

Jensen et al., "Estimation of the Blood Velocity Spectrum Using a Recursive Lattice Filter," IEEE Int'l. Ultrasonics Symposium, San Antonio, 1996.

Ikoma et al, "Adaptive Order Selection with Aid of Genetic Algorithm," IEEE Int'l. Fuzzy Systems Conf. Proc., Seoul, Korea, 1999.

* cited by examiner

ULTRASOUND CLUTTER FILTERING WITH ITERATIVE HIGH PASS FILTER SELECTION

CROSS-REFERENCE TO RELATED APPLICATIONS

This application is a continuation and claims the priority benefit of U.S. patent application Ser. No. 10/167,606 for a "System and Method for Adaptive Clutter Filtering in Ultrasound Color Flow Imaging" filed Jun. 11, 2002 and now U.S. Pat. No. 6,733,455; U.S. patent application Ser. No. 10/167,606 is a continuation-in-part of U.S. patent application Ser. No. 10/081,542 for a "User Interface for Handheld Imaging Devices" filed Feb. 20, 2002 and now abandoned which is a continuation-in-part of U.S. patent application Ser. No. 09/860,209 for a "Miniaturized Ultrasound Apparatus and Method" filed May 18, 2001 and now U.S. Pat. No. 6,569,102 which is a continuation of U.S. patent application Ser. No. 09/378,175 for a "Miniaturized Ultrasound Apparatus and Method" filed Aug. 20, 1999 and now U.S. Pat. No. 6,251,073; U.S. patent application Ser. No. 10/167,606 also claims the priority benefit of U.S. provisional patent application No. 60/370,632 for "Broad-Beam Imaging" filed Apr. 5, 2002.

This application is related to U.S. patent application Ser. No. 10/039,910 for a "System and Method for Coupling Ultrasound Generating Elements to Circuitry" filed Oct. 20, 2001 and U.S. patent application Ser. No. 10/101,661 for a "System and Method for Post-Processing Ultrasound Color Doppler Imaging" filed Mar. 19, 2002 and now U.S. Pat. No. 6,663,567.

The above-related applications are commonly assigned and are incorporated herein by reference.

FIELD OF THE INVENTION

This invention relates to filtering in general and to filtering ultrasound data in particular.

DESCRIPTION OF THE PRIOR ART

Ultrasonic imaging is a frequently used method of analysis for examining a wide-range of media and objects. Ultrasonic imaging is especially common in medicine because of its relatively non-invasive nature, low cost, and fast response times. For example, ultrasonic imaging is commonly used to detect and monitor the growth and health of fetuses, or to detect and assist in the diagnosis of liver and kidney pathology. Typically, ultrasonic imaging is accomplished by generating and directing ultrasonic sound waves (an ultrasonic beam or signal) into a medium under investigation using a set of ultrasound generating transducers and then observing reflections generated at the boundaries of dissimilar materials, such as tissues within a patient, also using a set of ultrasound receiving transducers. The generating and receiving transducers may be arranged in arrays and a single transducer may be used for both generating and receiving ultrasonic signals. The reflections are converted to electrical signals by the receiving transducers and then processed, using techniques known in the art, to determine the locations of echo sources. The resulting data is displayed using a display device, such as a monitor.

Typically, the ultrasonic signal transmitted into the medium under investigation is generated by applying continuous or pulsed electronic signals to an ultrasound generating transducer. In diagnostic imaging, the transmitted ultrasonic signal is generally in the radio frequency (RF) range of 1 MHz to 15 MHz, which corresponds to ultrasonic wavelengths in the range of 0.1 mm to 1.5 mm. The ultrasonic signal propagates through the medium under investigation and reflects off interfaces, such as boundaries, between adjacent tissue layers. Scattering of the ultrasonic signal refers to the deflection of the ultrasonic signal in many directions by interfaces that are much smaller than the ultrasonic wavelength. Attenuation of the ultrasonic signal is the loss of ultrasonic signal as the signal travels. Reflection of the ultrasonic signal is the bouncing off of the ultrasonic signal from an object (e.g., a vessel wall) that is similar in size or larger than the ultrasonic wavelength. Transmission of the ultrasonic signal is the passing of the ultrasonic signal through a medium. As it travels, the ultrasonic signal is scattered, attenuated, reflected, and/or transmitted. The portions of the reflected and/or scattered ultrasonic signals that return to the transducers are detected as echoes.

In the ultrasound art, steering refers to changing the direction of an ultrasonic beam. Aperture refers to the size of the transducer or group of transducer elements being used to transmit or receive an ultrasonic signal. The transmit aperture is the size of the transducer or group of transducers used to transmit an ultrasound signal, and receive aperture is the size of the transducer or group of transducers used to receive an ultrasound signal. Apodization refers to applying a weighting profile to the signals across the transducer aperture to produce ultrasound beams with reduced sidelobe spreading. Electronic focusing refers to applying relative time and/or phase shifts to signals across the transmit or receive transducer array elements to account for time-of-flight differences.

A conventional process of producing, receiving, and analyzing an ultrasonic signal (or beam) is called beam forming. The production of ultrasonic signals optionally includes apodization, steering, focusing, and aperture control. In conventional beamforming, RF echo data is acquired across a transducer array and processed to generate a one-dimensional set of echolocation data. In a typical implementation, a plurality of ultrasonic beams are used to scan a multi-dimensional volume.

In electronic focusing, the transmit aperture of the transducer is apodized and electronically focused to form a transmit beam, and a large number (typically over 100) of transmit beams are generated and steered (as for a sector scan) along different scan lines to cover the entire scan plane.

To create two-dimensional (2D) B-mode images of tissue and 2D color flow images of moving blood, the echoes are detected and converted into electronic signals by the receive transducer aperture elements. Through parallel electronic channels the signals in different frequency bands are subject to amplification, digitization, frequency downshifting, apodization, focusing, steering and other filtering operations in order to generate echolocation data along the scan direction. Depending on the front-end architecture design, the order in which the above processing are performed may vary. Any processing such as amplification, which occurs before digitization would be implemented using analog electronic circuits.

In most ultrasound receivers, the echo signals are shifted down in frequency by means of frequency mixers and filters, to generate the in-phase (I) and quadrature (Q) signals which are centered at a much reduced RF frequency, but contain the same information. bandwidth as the RF signals. For color flow processing, the RF spectrum is shifted down to baseband and the resultant I/Q components are also referred to as baseband components. The advantage of using I/Q echo components is that they can be digitized and processed at much lower sampling rates due to their reduced Nyquist bandwidths.

The I/Q echo data is furnished to the B-mode and color flow image processors for amplitude and motion detection respectively. For B-mode, the echo amplitude can be computed simply by taking the square root of $I^2+Q^2$. The detected data from different transmit events are compiled into 2D acoustic data sets, which are then converted by the scan-converter into X-Y format of, for example, 480×640 pixels (picture elements), for video display.

In B-mode imaging, the brightness of a pixel is based on the detected echo amplitude, whereas in color flow imaging, the color of a pixel is based on mean velocity and/or power of detected echoes from moving parts of the medium under investigation. In color flow imaging, the color flow image is formed within a region of interest (ROI), which is over-written onto the B-mode image by a video image processor such that, for example, the composite image depicts blood flow within the ROI according to a color scale, while surrounding stationary tissues are displayed in a gray-scale.

In color flow imaging, for each scan line within the user-specified ROI, a set of transmit beams are fired repeatedly at some pulse repetition frequency (PRF), in order to detect moving blood. Fundamentally, any motion of the medium under investigation relative to the ultrasound transducer produces the well-known Doppler effect in which the frequency of the reflected echo is shifted from that of the transmit frequency $f_o$ by an amount $f_d$ that is proportional to the target speed in the direction of the ultrasonic beam. That is, the frequency of the reflected signal is $f_o+f_d$. A medium under investigation that is moving towards the transducer will compress the incident ultrasonic wave thereby producing a positive Doppler frequency shift in the reflected echo. Conversely, a target that is moving away from the transducer will produce a negative Doppler frequency.

Mathematically, the Doppler frequency shift $f_d$ can be derived as follows. Suppose the target (e.g. red blood cells) is moving at velocity v, which makes an angle $\phi$ with respect to the sound beam. This means that the target velocity component in the direction of the sound waves is $u=v \cos(\phi)$. Over a short time interval $\Delta t$, the change in round-trip distance between the target and the ultrasonic source (transducer) is $\Delta d=2u\Delta t$. Assuming u<<c (speed of sound), $\Delta d$ translates into a phase shift $\Delta\theta=2\pi\Delta d/\lambda$, where $\lambda=c/f_o$ is the ultrasound wavelength. Hence, the Doppler frequency shift induced by target motion is $$f_d=\Delta\theta/(2\pi\Delta t)=2f_o(u/c)=2f_o(v/c)\cos(\phi).$$

In practice, Doppler frequencies due to blood flow in humans and animals are in the kHz range, which are much smaller than the transmit radio frequencies. A minimum of two transmit signals must be fired along each scan line in order to generate a measurable phase change between the returning echoes from two successive firings. At a Pulse Repetition Interval (PRI)=1/Pulse Repetition Frequency (PRF), the phase change between echoes from two successive firings is $\Delta\theta=2\pi f_d$/PRF. Color image processors create a color velocity image by estimating $\Delta\theta$ for each acoustic point, and then converting it into either Doppler frequency or velocity unit, which is then mapped to a 2D pixel display image according to a color versus velocity or Doppler frequency scale.

Since the instantaneous phase of the returning RF echo from each transmission of an ultrasonic beam is equivalent to the angle of its baseband I and Q components; i.e., $\theta=\tan^{-1}(Q/I)$, the phase change over two successive transmit and receive cycles is simply given by $$\Delta\theta=\tan^{-1}(Q_1/I_1)-\tan^{-1}(Q_2/I_2).$$

In practice, there are two significant challenges in producing a real-time color flow image. First, the echoes returning from moving blood are generally very weak, so typically a packet of several or more transmit and receive cycles are needed to detect flow along a particular scan line. Color Doppler velocity estimation then involves computing the mean phase change <$\Delta\theta$> per PRI from the received echo signals. As will be defined in a later section, a common method of estimating <$\Delta\theta$> is to evaluate the first-ordered autocorrelation function of $\{I_n,Q_n\}$ over the transmit packet (n=1, 2, 3 . . . ) for each acoustic point in the medium under investigation. In other words the autocorrelation is between all possible pairs of $\{I_n,Q_n\}$ and $\{I_m,Q_m\}$ at the same position, where n and m represent different time indices within a color Doppler data packet.

The second practical challenge stems from the fact that the tissue medium, and especially bones and tissue layers that comprise the vessel walls of the insonified blood vessel, often produce very strong reflections that are orders of magnitude larger than the backscattered signals from blood. Without first removing the clutter, the I/Q data analysis would be dominated by clutter effects and will not reflect the desired flow signal properties. To compound this problem, the reflecting structures in the medium under investigation (such as the body) are often moving at low velocities (due to breathing and/or cardiac motion, for example), which means the corresponding clutter signals may also contain Doppler frequency components or phase changes that can register as "color flashes" in the color flow image.

In order to provide a common framework for understanding the clutter problem, and the new and existing solutions, it is helpful to visualize (FIG. 1) the flow signal component and any unwanted DC or low-frequency clutter component in the Doppler frequency domain (even though color flow image processors don't actually need to compute the Doppler frequency spectrum from the input I/Q data.)

FIG. 1 is a plot 100 of spectra of clutter and flow components, and a High Pass Filter (HPF) frequency response. FIG. 1 shows frequency spectra of color flow I/Q data having a clutter spectrum 102, and a flow signal spectrum 104, and a HPF frequency response (HPF1) 106 plotted on an x-axis 108 and y-axis 110. X-axis 108 is in units of Hertz (Hz), and y-axis 110 is in units of decibels (dB). The signal spectra 102 and 104 are normalized in magnitude such that the clutter spectrum peak is 0 dB. For the HPF response HPF1 106, 0 dB means the filter gain is unity at that particular frequency. In general, clutter spectrum 102 could be the frequency spectrum of a stationary object (such as a bone) and/or of the relatively slow motion of other objects within the medium under investigation. For example, clutter spectrum 102 in FIG. 1 represents the reflected signal that contains a very low Doppler frequency spectrum ranging from 0 to about 30 Hz, with the peak at about 15 Hz. Flow spectrum 104 represents the frequency spectrum of a typical flow from a fluid such as blood within a medium under investigation.

In the body, tissue motion may be caused by breathing, cardiac motion, or simply transducer motion due to the operator, which are generally of a lower speed than blood flow in detectable vessels. The average power of the clutter may be up to 40 dB stronger than the flow signal in the time domain, so that the peak of clutter spectrum 102 may be 50 dB higher than that of flow spectrum 104.

Three approaches to clutter removal in conventional color flow imaging include using a High Pass Filter (HPF), using a Fast Fourier Transform (FFT), and using a clutter model. These are summarized as follows:

When using a HPF, having for example frequency response HPF1 106, the ultrasound signal from the transducer is passed through a linear high pass Finite Impulse Response (FIR) or Infinite Impulse Response (IIR) filter in the time domain. A high pass filter response such as HPF1 106 shows which frequency band is attenuated, and which frequency band is allowed to pass. The amplitude of the signal component at a given frequency is reduced by the HPF1 106 response (e.g. −50 dB) at that frequency. For example at 460 Hz, the signal amplitude is reduced by −8 dB or about 40%. In the frequency domain, clutter spectrum 102 tends to concentrate around the lowest frequency bins. HPF1 106 is effective for rejecting the relatively low frequency clutter spectrum 102.

In FIG. 1, HPF1 106 corresponds to the frequency response of a filter whose −50 dB stopband edge is at a normalized frequency (ie., a frequency divided by PRF/2) of 10%.

When using an FFT, the FFT is taken of basebanded I/Q data samples and then the power in the lowest frequency bins is set to zero. This can be viewed as frequency-domain filtering, or a form of clutter modeling in which the data is projected onto a series of complex exponentials of various Doppler shift frequencies.

When using a clutter model (see, e.g., U.S. Pat. No. 5,228,009 incorporated herein by reference) the part of data samples that represent the clutter (e.g., the time domain representation of clutter spectrum 102) is projected onto a set of low order orthonormal basis functions (e.g., legendre polynomials), thereby forming a model or fitted curve of the clutter. Then the sum of projections (i.e., the fitted curve) is subtracted from the data samples thereby subtracting the modeled clutter from the data. Using the low frequency components of a frequency spectrum (which may have been obtained via an FFT) to represent the clutter is a special case of clutter modeling.

In all the above three approaches, appropriate parameters are selected that depend on the tissue velocity, such that only the clutter and not the blood flow signal is subtracted from the data or suppressed. Choosing the appropriate parameters is equivalent to choosing the cutoff frequency (and the order) of the high pass filter or to selecting the highest order for the basis functions in the clutter modeling approach. If the filter cutoff is always set high to reject the highest possible clutter frequencies, then some low flow signals may not be detected well. If the filter cutoff frequency is always set low, color flashes may result in the image whenever significant clutter power due to tissue motion is present above the cutoff frequency. Hence, various adaptive clutter suppression techniques have been proposed in the prior art as follows.

U.S. Pat. No. 6,309,357 uses two or more clutter filters of different frequency responses to process each color data packet in parallel and then select or combine the best results for velocity estimation. U.S. Pat. Nos. 5,349524 and 5,445,156 estimate clutter velocity and bandwidth using the standard autocorrelation method, and then either shift the clutter frequency down to DC before high pass filtering, or apply a complex filter with a notch at the estimated clutter frequency. U.S. Pat. No. 5,349,525 estimates the clutter velocity and bandwidth and excise the corresponding bins in the FFT spectrum of the data. U.S. Pat. No. 5,228,009 starts with the lowest order of basis functions (mean removal), computes and subtracts projections from the data onto the basis functions, and then checks the residual energy. The process is repeated for the next lowest order until residual energy falls below a predefined threshold.

In U.S. Pat. Nos. 5,349524, 5,349,525, and 5,445,156, the velocity estimation is performed twice for each packet or acoustic point in the color flow image. Specifically, the velocity estimation is performed the first time to estimate mean clutter velocity, and the second time to estimate the mean flow velocity after the clutter has been subtracted out. Also, the standard autocorrelation method involves a division and an arctangent operation, which are computationally expensive. In U.S. Pat. No. 5,228,009, as the order of filtering increases, the amount of computations required for computing the projection onto the basis function based on the least squares criterion also increases and is quite computationally intensive.

In U.S. Pat. No. 5,782,769, a high pass filter suitable for clutter from non-moving sources is applied prior to velocity estimation, and a separate nonlinear "min-max" filter is used across image frames to suppress color flashes that may result from tissue motion. While it is true that in general, color flashes can be rejected by such post processing or other simpler threshold techniques based on the total power and mean velocity estimates, if a weaker flow signal is also present, it will likely get thrown out with the flash artifact.

SUMMARY OF INVENTION

An adaptive clutter removal method is provided that can suppress color flash artifacts without compromising low flow detection. The method utilizes an adaptive high pass filter which is applied to the in-phase (I) and quadrature (Q) components of a given flow data packet prior to flow parameter estimation. The clutter may be detected and the cutoff frequency may be adjusted iteratively, may be adjusted on a point-by-point or region-by-region basis, and may be adjusted dynamically or in real time, while collecting the data for other acoustic points. For example, in an embodiment while data for one frame is imaged, a second frame is filtered, and a third frame is collected.

In an embodiment two criteria are used to detect the clutter, which are the magnitude of the total signal power being higher than a given threshold and the mean Doppler frequency (proportional to mean velocity) being lower than a given clutter frequency threshold. Ordinarily, calculating the mean frequency or phase change entails taking an arc tangent of the real and imaginary parts of the first order autocorrelation function of the I/Q data. However, determining whether the mean frequency change is less than a threshold does not require actually calculating the mean frequency change. Instead, in an embodiment, a check is performed to see if the real part times a multiplicative factor is greater than the absolute value of the imaginary part of the first order autocorrelation function. The multiplicative factor is determined by the ratio of a clutter frequency threshold to the pulse repetition frequency.

Although the method is equally applicable to I/Q flow data derived from 2D or 3D volume scanning based on conventional line-by-line beam forming, the preferred embodiment, for which this is a continuation-in-part, is referred to as area forming which is enabled by broadbeam technologies. Broad beam technologies refer to systems and methods that include or take advantage of techniques for generating a broad ultrasound beam from a single ultrasonic pulse, and analyzing the returning echoes to yield multidimensional spatial information.

The receive system architecture for the preferred broad beam system utilizes software running on a set of Digital Signal Processing (DSP) chips to perform all of the image processing operations after area forming. Although the adaptive clutter filter can also be implemented in hardware, the programmability and scalability of DSP chips provide an ideal match to the algorithmic nature of the adaptive clutter filter. For example, to achieve more optimal clutter filter performance, the number of iterations and high pass filter choices can be increased in concert with technological advances in the DSP chip family.

Area forming is the process of producing, receiving, and analyzing RF echoes from a medium under investigation, that optionally includes apodization, steering, focusing, and aperture control, where a two-dimensional set of echolocation data can be generated using only one ultrasonic beam. Nonetheless, more than one ultrasonic beam may still be used with the area forming even though only one is necessary. Area forming is a process separate and distinct from beam forming. Area forming may yield an area of information using one transmit and/or receive cycle, in contrast to beam forming, which typically only processes a line of information per transmit and/or receive cycle.

Volume forming is the process of producing, receiving, and analyzing an ultrasonic beam, that optionally includes apodization, steering, focusing, and aperture control, where a three dimensional set of echolocation data can be generated using only one ultrasonic beam. Nonetheless, multiple ultrasonic beams may be used although not necessary. Volume forming is a superset of area forming.

Multidimensional forming is the process of producing, receiving, and analyzing an ultrasonic beam that optionally includes apodization, steering, focusing, and aperture control. Using multidimentional forming a two or more dimensional set of spatial echolocation data can be generated with only one ultrasonic beam. Nonetheless, multiple ultrasonic beams may be used although not necessary. Multidimensional forming optionally includes non-spatial dimensions such as time and velocity.

DETAILED DESCRIPTION OF THE INVENTION

Figure 2:
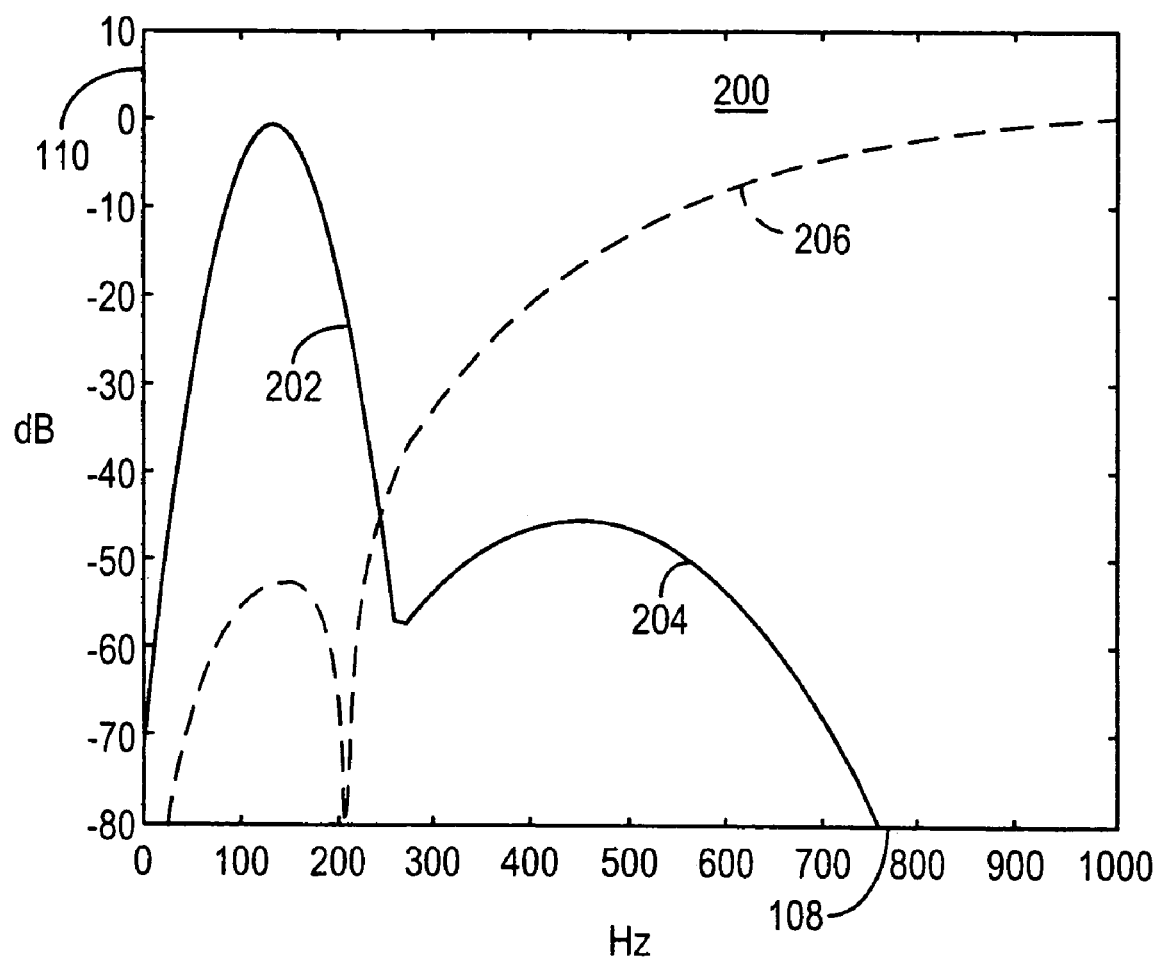
FIG. 2 is a plot of spectra of another clutter and flow components, and another HPF frequency response.

FIG. 2 is another plot 200 of spectra of clutter and flow components of a color flow I/Q data packet having a clutter spectrum 202, a flow spectrum 204, and a high pass filter frequency response (HPF2) 206 plotted on an x-axis 108 and y-axis 110.

Figure 1:
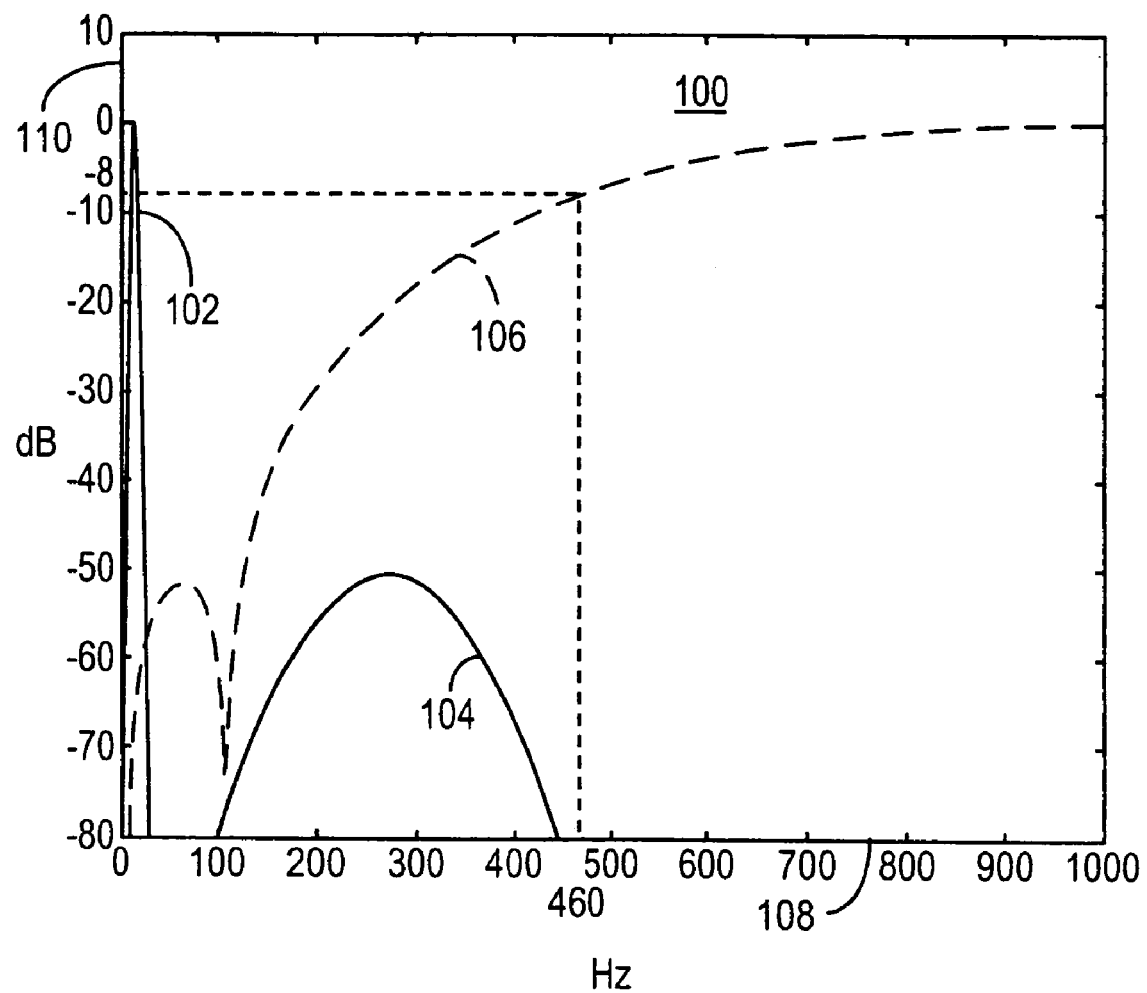
FIG. 1 is a plot of spectra of clutter and flow components, and a HPF frequency response.

In contrast to HPF1 106 of FIG. 1, FIG. 2 shows HPF2 206 with a stopband cutoff frequency of 20%, which is needed to suppress a higher velocity clutter associated with tissue motion. Clutter spectrum 202 represents moving tissue such as a pumping heart and therefore has an overall higher frequency spectrum than that of clutter spectrum 102 (FIG. 1). Flow spectra 204 and 104 (FIG. 1) differ in their distribution of frequencies. Flow spectrum 204 is broader than flow spectrum 104 and overlaps with clutter spectrum 202. HPF2 206 has a higher cutoff frequency than HPF1 106 (FIG. 1), whereas flow spectrum 104 represents a lower velocity and has a lower mean frequency than flow spectrum 204. The selection of the HPF should be made so as to remove clutter spectrums 102 or 202 without significantly affecting flow spectrums 104 or 204. However, in plot 200 it is unclear exactly where the cutoff frequency should be because of clutter spectrum 202.

In conventional ultrasound systems, the wall (or clutter) filter cutoff frequencies of the HPF can be manually selected via front panel controls. In practice, however, the tissue motion often varies over the cardiac or breathing cycle, and from region to region within the color flow image. If, as in FIG. 2, the wall filter cutoff frequency is always set low, "color flashes" (regions having heavy concentrations of low frequency I/Q data) may result in the image whenever significant clutter power is present (i.e., some is present above the cutoff frequency). Although it is possible to suppress color flashes by threshold techniques based on the total power and mean velocity estimates, if a weaker flow signal is also present, it may get thrown out together with the flash artifact.

Figure 3:
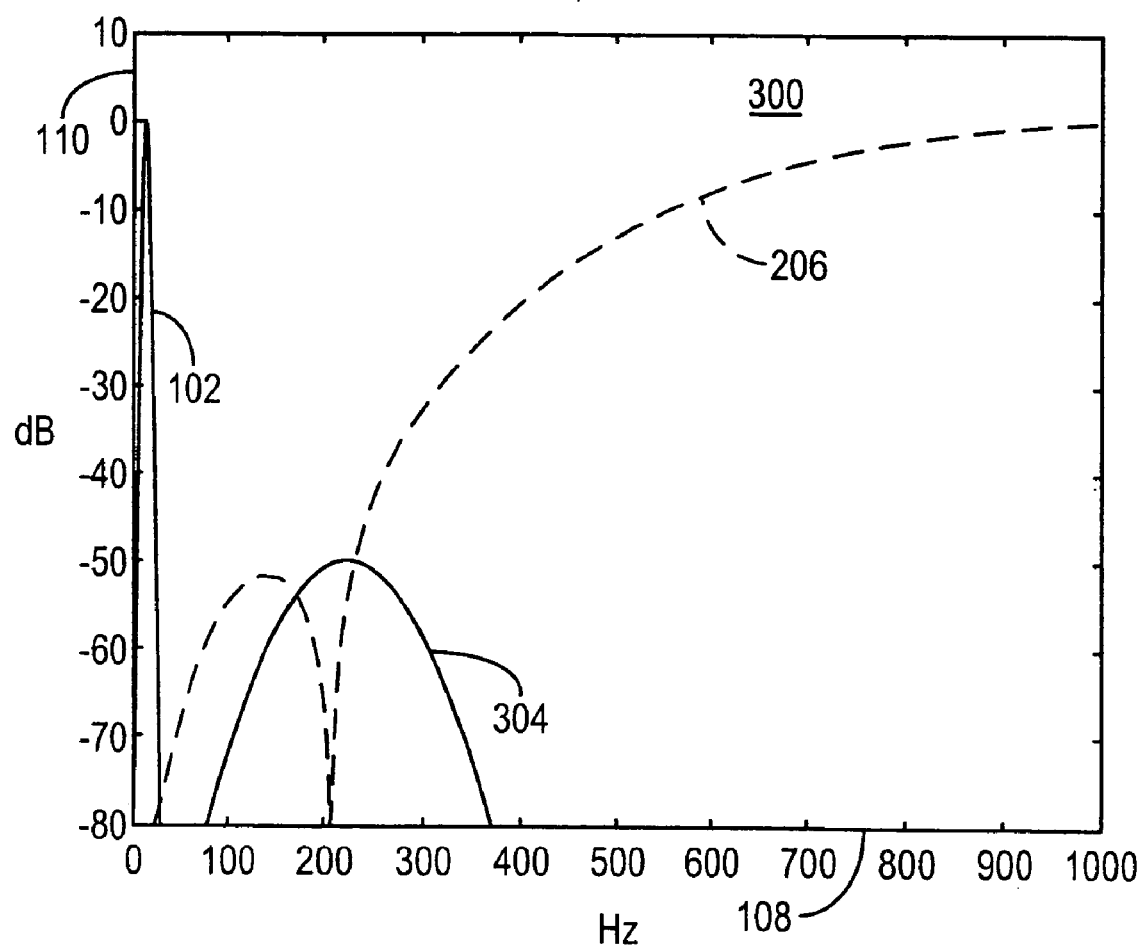
FIG. 3 is a plot of spectra of a color flow I/Q data packet, and another HPF frequency response.

FIG. 3 is another plot 300 of spectra of the flow and clutter components of a color flow I/Q data packet showing a clutter spectrum 102, a flow spectrum 304, and high pass filter frequency response (HPF2) 206 plotted on an x-axis 108 and y-axis 110. FIG. 3 shows a situation in which low flow will be largely missed because of the high cutoff frequency of HPF2 206. In contrast to the effectiveness of HPF1 106 with respect to flow spectrum 104 or HPF2 206 with respect to flow spectrum 204, HPF2 206 would not be appropriate for flow spectrum 304 because it significantly attenuates flow spectrum 304 rather than leaving it relatively unaffected. Although HPF2 206 may be appropriate for acoustic points in parts of the image or some periods of time in which clutter spectrum 102 has a relatively high velocity, if the cutoff frequency remains high even when the clutter frequencies (e.g., clutter spectrum 102) are at a later time or in a different part of the image near zero, low frequency flow information is lost.

Figure 4:
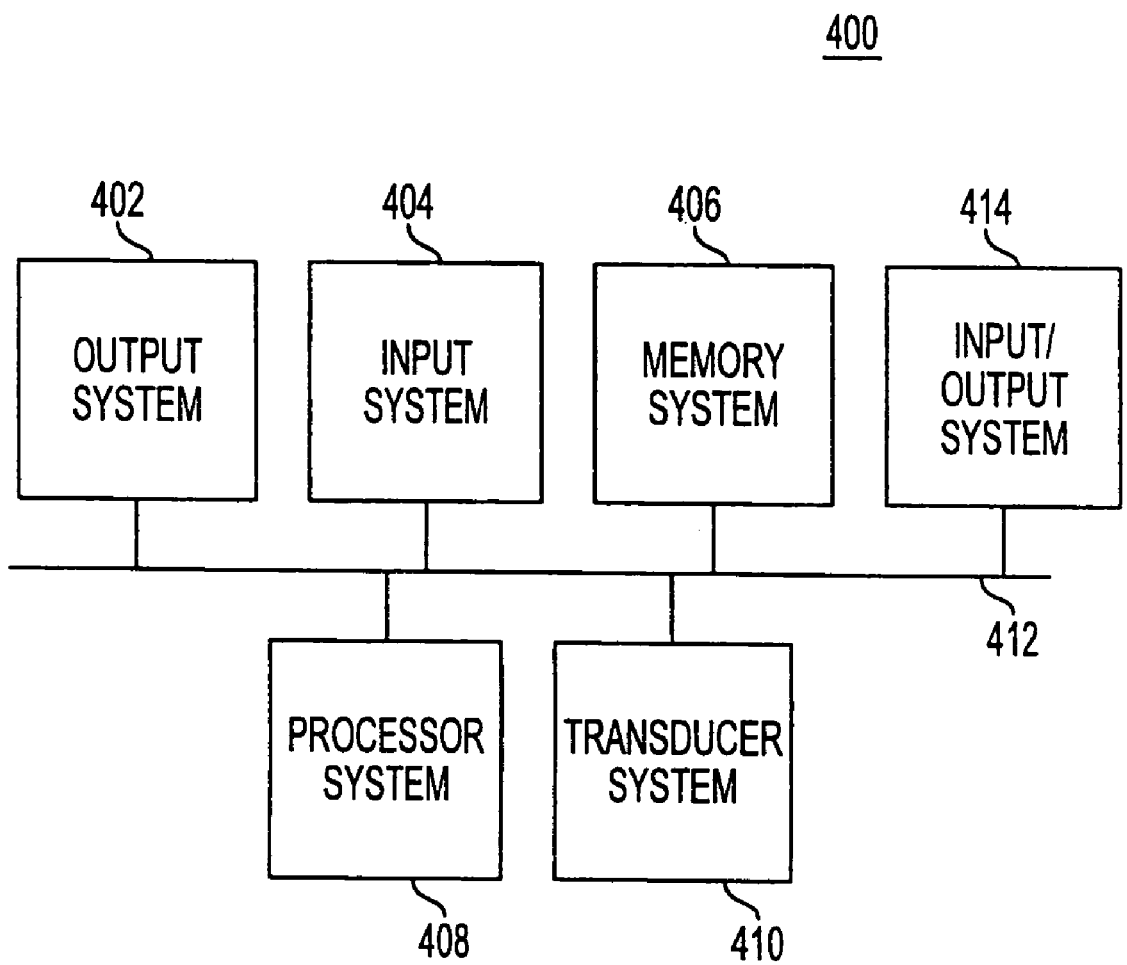
FIG. 4 is a block diagram of one embodiment of an ultrasound system.

FIG. 4 is a block diagram of an ultrasound system 400 according to an embodiment of the invention including an output system 402, an input system 404, a memory system 406, a processor system 408, a transducer system 410, a communications system 412, and an input/output system 414.

Output system 402 may include any one of, some of, any combination of, or all of a monitor system, a handheld display system, a printer system, a speaker system, a connection or interface system to a sound system, and/or a connection and/or interface system to a computer system, intranet, and/or internet, or the like. Input system 404 may include any one of, some of, any combination of, or all of a keyboard system, a mouse system, a track ball system, a track pad system, buttons on a handheld system, a scanner system, a microphone system, a connection to a sound system, and/or a connection and/or interface system to a computer system, intranet, and/or internet or the like.

Input/output system 414 includes devices and/or systems that are both input and output devices such as a touch sensitive screen in which output is displayed on the screen and input is entered by touching the screen. Input/output system 414 is optional and may be in addition to or may replace input system 404 and/or output system 402. Memory system 406 may include, for example, any one of, some of, any combination of, or all of a long term storage system, such as a hard drive; a short term storage system, such as random access memory; a removable storage system, such as a floppy drive or a removable drive; and/or flash memory. Processor system 408 may include any one of, some of, any combination of, or all of multiple parallel processors, a single processor, a system of processors having one or more central processors and/or one or more specialized processors dedicated to specific tasks. Transducer system 410 may include any one of, some of, any combination of, or all of one or more transducers, linear arrays of transducer elements, and/or two-dimensional arrays of transducer elements. A different group of transducer elements may be chosen from the same array to obtain an image of a different aperture and/or different perspective. Transducer system 410 may also include acoustical systems for guiding and/or focusing the ultrasound beam, for example. Transducer system 410 may include antireflection layers and/or filters for filtering out noise, for example. Processor system 408 may include one or more specialized processors for controlling transducer system 410 and/or processing signals and/or data received by transducer system 410. An example of the construction of transducer system 410 is shown in U.S. patent application Ser. No. 10/039,910—publication number US 2002-0138002 A1—for a "System and Method for Coupling Ultrasound Generating Elements to Circuitry" filed Oct. 6, 2001.

Communications system 412 communicatively links output system 402, input system 404, memory system 406, processor system 408, and transducer system 410 to each other. Communications system 412 may include any one of, some of, any combination of, or all of electrical cables, fiber optic cables, and/or means of sending signals through air or water, or the like, and may include the cableless connector of U.S. patent application Ser. No. 10/039,910. Some examples of means of sending signals through air and/or water include systems for transmitting electromagnetic waves such as infrared and/or radio waves and/or systems for sending sound waves.

Figure 5:
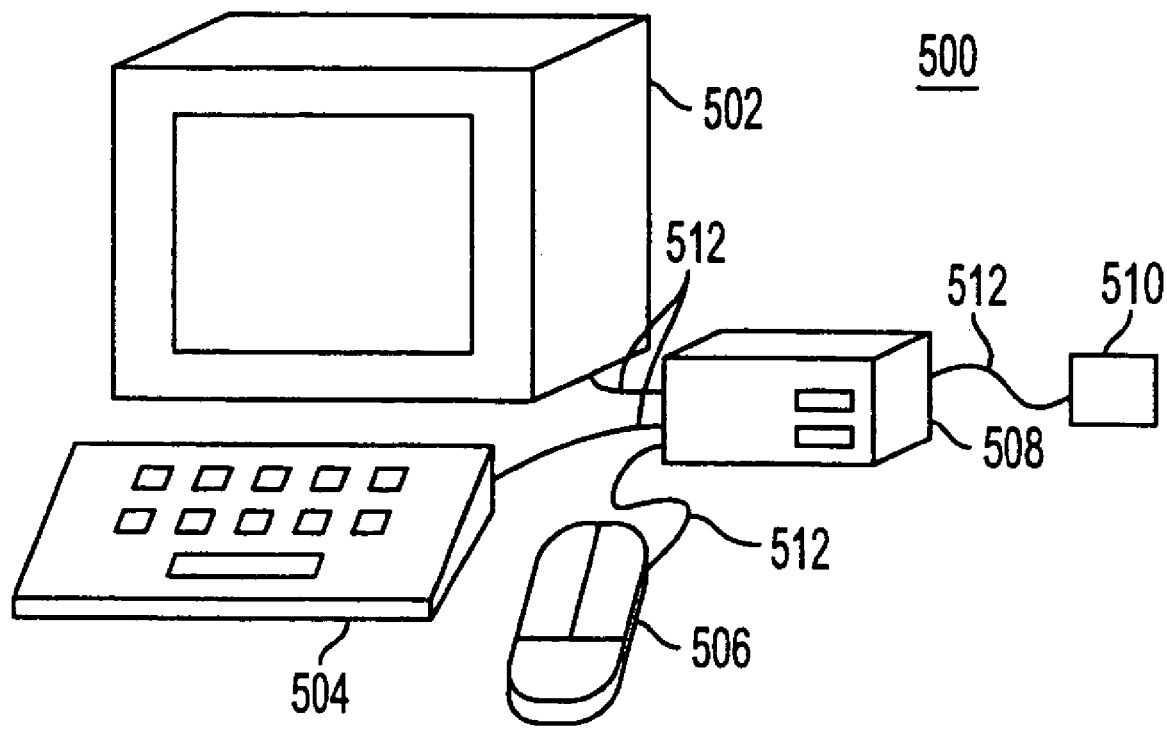
FIG. 5 shows an embodiment of the ultrasound system of FIG. 4.

FIG. 5 shows an embodiment 500 of ultrasound system 400 having a monitor 502, a keyboard 504, a mouse 506, a computing system 508, a transducer system 510, and cables 512. Monitor 502 may be touch sensitive or may be just for viewing. Monitor 502 is part of output system 402 (FIG. 4). If monitor 502 is touch sensitive, it is part of input/output system 414 (FIG. 4). Keyboard 504 and mouse 506 are part of input system 404 (FIG. 4), and are used to input text and/or select menu items, icons, virtual tabs and/or virtual buttons, for example. Computing system 508 includes processing system 408 and memory system 406 (FIG. 4). Transducer system 510 is part of transducer system 410, and is used for transmitting (generating and receiving) ultrasound signals to a medium under investigation such as a human body.

Figure 6:
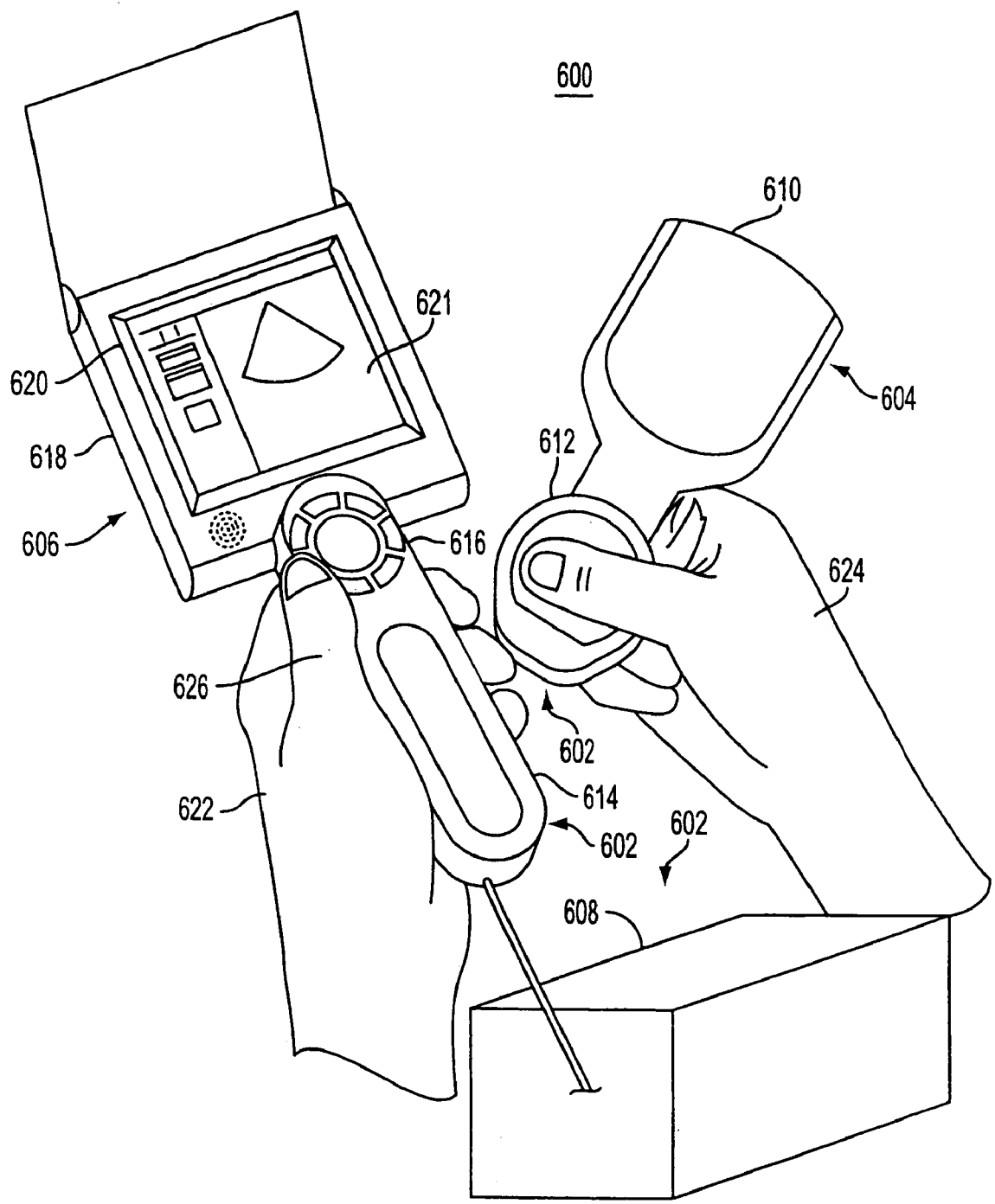
FIG. 6 shows another embodiment of the ultrasound system of FIG. 4.

FIG. 6 shows another embodiment 600 of ultrasound system 400. Embodiment 600 has an imaging unit 604, a display and control unit 606, which may also be referred to as a Processing and Display Unit (PDU), and a docking unit 608. Imaging unit 604 includes an imaging module 610 and a transducer module 612. Display and control unit 606 includes two parts which are (1) a handle 614 having buttons 616 and (2) a monitor module 618 having a screen 620 displaying a GUI 621. Embodiment 600 uses hands 622 and 624.

Embodiment 600 is a hand-held device that can be operated with either hand 622 or 624. Ultrasound system 400 may be any type of handheld ultrasound imaging unit, such as that of U.S. Pat. No. 6,251,073.

Display and control unit 606 may be responsible for setting up, displaying, processing, storing, and annotating information gathered from imaging unit 604. The function of display and control unit 606 may include image reconstruction, color flow estimation, and Doppler computations, for example. Display and control unit 606 may include a Personal Digital Assistant (PDA). Display and control unit 606 may be battery operated, and screen 620 on display and control unit 606 may be touch sensitive. Handle 614 is for holding display and control unit 606. User interactions with display and control unit 606 may be through buttons 616 on handle 614 and/or touch sensitive control areas on screen 620. In an embodiment (not shown), handle 614 could be replaced with a small keyboard or panel having buttons 616. Screen 620 displays GUI 621, which may have views of fixed formats and/or may give the user the option to retile or rearrange the windows of GUI 621 on the screen in any fashion desired.

In addition to a location for storing imaging unit 604 and/or display and control unit 606, docking unit 608 may be used for recharging imaging unit 604 and/or display and control unit 606. Alternatively, docking unit 608 may also be used for downloading and/or uploading files to display and control unit 606. Alternatively, docking unit 608 may be used for both recharging and uploading and/or downloading files.

Imaging module 610 processes received RF echo data and converts it into a format that facilitates image processing by display and control unit 606. Imaging module 610 is responsible for collecting and digitizing ultrasound data. Imaging module 610 also produces the signals to control and/or drive the transducers of the transducer array of transducer module 612.

Transducer module 612 includes an imaging ultrasound scan head having an array of transducer elements used to transmit ultrasound signals for data acquisition. Transducer module 612 converts electrical signals into acoustic signals and acoustic signals into electrical signals, for the purpose of transmitting and receiving the ultrasound information.

Monitor module 618 and any means, such as docking unit 608, of outputting information to a printer on another computer is part of output system 404 (FIG. 4). Buttons 616 and any means of inputting data (e.g., patient information or images) from a computer system or database is part of input system 402 (FIG. 4). Imaging module 610 and any processing and/or memory units within display and control unit 606 may include parts of or all of memory system 406 (FIG. 4) and/or processing system 408 (FIG. 4). Transducer module 612 is part of transducer system 410 (FIG. 4). If screen 620 is touch sensitive it can be included in input/output system 414. The cables and/or means for communicating through the air (using electromagnetic or sound signals) are part of communication system 412 (FIG. 4).

In one embodiment (not shown), screen 620 and buttons 616 are located in different units. Buttons 616 could be placed on imaging unit 604. Imaging module 610 and transducer module 612 do not have to be placed in the same unit. Imaging module 610 could be placed in the same unit with screen 620 and buttons 616, or could be placed with only screen 620, while buttons 616 are on the same unit as only transducer module 612. Alternatively, imaging unit 604 and display and control unit 606 could be placed together in one unit. The invention is not limited to a handheld system. Display and control unit 606 could be replaced with an appliance that is not handheld such as a laptop computer, personal computer, workstation, or mainframe computer, which may or may not include imaging module 610. The appliance that is not handheld (e.g., a computer) may be programmed to perform the functions of imaging module 610 and display and control unit 606.

Embodiments 500 and 600 or any embodiment of ultrasound system 400 may provide a user interface that may include several intelligent (adaptive and context sensitive) active elements, e.g., windows, soft buttons, tabs, menus, toolbars, and/or icons.

In one embodiment, GUI 621 interface is voice controlled, and the user can train the device to recognize a set of words or combinations of words. Each recognizable unit (word or word combination) can be assigned to a device command, performing a specific function or a sequence of functions. Some or all functions can be voice activated obviating or partially obviating the use of hand controls. A similar GUI can be provided for embodiment 500 or any of the embodiments of ultrasound system 400.

Figure 7A:
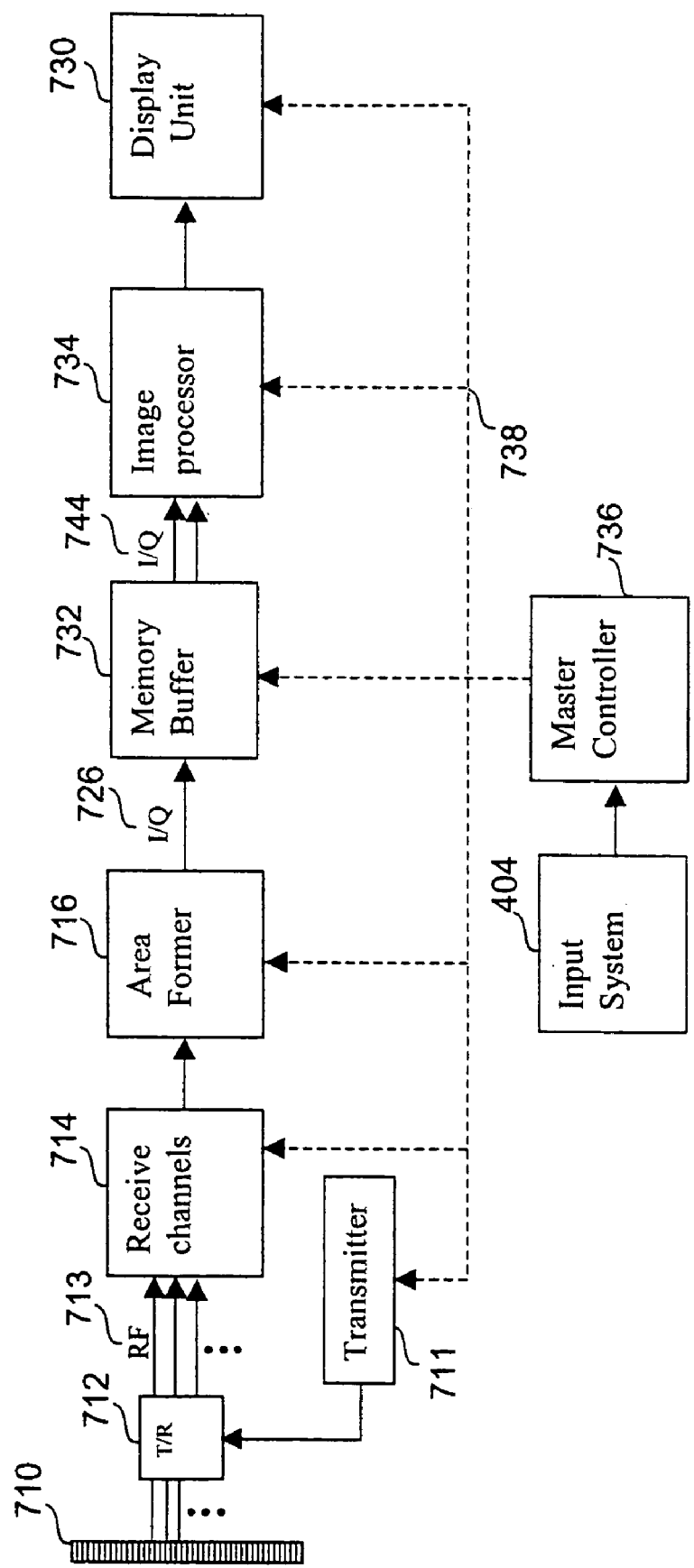
FIG. 7A is the main system block diagram for the ultrasound system of FIG. 5 or FIG. 6.

FIG. 7A shows the main system block diagram 700 for an embodiment of ultrasound system 400 that supports B-mode and color flow imaging, input system 404, having a transducer array 710, a transmitter 711, a T/R 712, RF data 713, electronic receive channels 714, area former 716, I/Q signals 726, display unit 730, memory buffer 732, image processor 734, master controller 736, and control signals 738.

Master controller 736 receives and interprets inputs from the user, for example via input system 404, and sends control signals 738 (dashed lines) to activate and coordinate the functions of various subsystems in order to effect the changes requested by input system 404. In an embodiment master controller 736 may include control software running on a microprocessor.

T/R 712 represents hardware switches that connect transducer array 710 to either transmitter 711 or receive channels 714. For example, during a transmit event, T/R 712 may connect transducer array 710 to transmitter 711, and during a receive event, T/R 712 may connect transducer array 710 to receive channels 714. The state of T/R 712 may be controlled through transmitter 711 as illustrated or directly by master controller 736.

Transmitter 711 produces the signals for causing transducer array 710 to produce, focus, and steer an ultrasound beam. Receive channels 714 are parallel analog circuits that amplify and filter the signals received from transducer elements that form the active receive aperture of transducer array 710.

In the ultrasound art the terms "insonation" and "insonify" refer to filling a volume with sound and are analogous to the optical terms "illumination" and "illuminate." In an embodiment of Broadbeam Technologies, a broad beam is generated by transmitter 711 and transducer array 710 to insonify an entire sector (in case of a phased array) or parallelogram (in case of a linear array) in a single transmission. After amplification and noise filtering of the received echo data in receive channels, area former 716 performs the receive apodization, beam steering and focusing operations on a point by point basis within the insonified area. Area former 716 also performs digitization and frequency downshifting operations to produce I/Q signals 726 having I/Q components of the 2D echolocation data for image detection and processing.

The I/Q data of I/Q signals 726 generated by area former 716 can be stored in memory buffer 732. Storing the I/Q data in memory buffer 732 is especially important in color flow imaging, in which a packet of, for example, 10 transmit pulses are repeatedly fired at some predetermined PRF depending on depth and velocity scale settings, to insonify each broad beam transmit zone. That is, for each acoustic point within a transmit zone, 10 I/Q data samples must be accumulated and stored in memory buffer 732 over a period of N/PRF (or more) to form a color packet of N I/Q points for color flow processing.

Image processor 734 may include one or more digital signal processing (DSP) chips that are dedicated to image processing for both B-mode and color flow. The DSP chip or chips allow image processor 734 to be highly programmable and re-configurable for real-time implementation of a wide range of algorithms including data-adaptive algorithms. Image processor 734 also performs scan conversion and video processing to produce raster scan or XY pixel data to form video or still images on display unit 730. The specific processing steps required for color flow imaging will be described in conjunction with FIG. 7B.

Transducer 710 is part of transducer system 410. Display unit 730 is part of output system 402. Control signals (dashed lines) are transmitted via parts of communications systems 412. Any part of, any one of, any combination of parts of, or all of transmitter 711, T/R 712, and/or receive channels 714, area former 716, memory buffer 732, image processor 734, and master controller 736 may be any one of or any combination of hardware, firmware, and/or software and may be included in any one of or any combination of transducer system 410, processor 408, and/or memory 406.

Figure 7B:
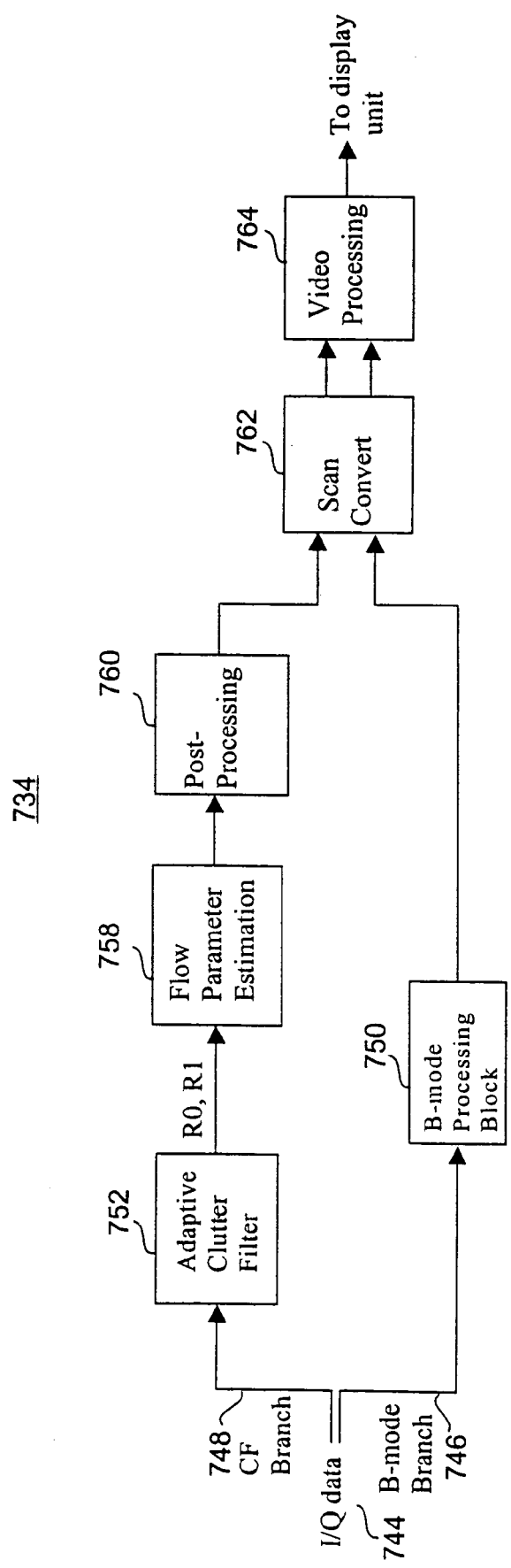
FIG. 7B is block diagram showing processing blocks that process the signal within the image processor of FIG. 7A.

FIG. 7B is a block diagram showing processing blocks that process the signal within image processor 734 for color flow and B-mode having I/Q data 744, B-mode branch 746, Color Flow (CF) branch 748, B-mode processing block 750, adaptive clutter filter 752, zeroth and first order autocorrelation estimates R0 and R1, flow parameter estimation 758, post processing 760, scan converter 762, and video processing 764.

Each block of FIG. 7B may represent parts of one or more software programs, firmware and/or circuitry dedicated for performing the function specified. Since B-mode may provide anatomical echo data surrounding the flow regions in a color flow image, some time may be allotted for B-mode transmit events and I/Q data 744 acquisition even during color flow imaging. I/Q data 744 is generated from I/Q signals 726. I/Q data 744 of B-mode branch 746 is fed into B-mode processing block 750, which includes magnitude detection, filtering, and log compression operations.

In the Color Flow (CF) branch 748, each packet of color flow I/Q data that corresponds to a specific acoustic point within the color ROI, is passed through adaptive clutter filter 752, which removes the clutter from slow moving or stationary sources in the medium under investigation such as a human body. Adaptive clutter filter 752 outputs the filtered I/Q data, and in the preferred embodiment, adaptive clutter filter 752 also outputs the zeroth and first order autocorrelation estimates R0 and R1, which can be used directly for flow parameter estimation 758 including flow signal energy, mean Doppler frequency/velocity, and flow velocity variance estimation, for example. Post processing 760 includes thresholding to reject estimates that may be corrupted by noise, and/or spatial and/or temporal filtering to enhance overall image quality. Both color flow and background B-mode acoustic image data are sent to scan converter 762 and are scan converted based on the known scan format, to produce XY (raster scan) pixel data. Video processing 764 includes combining the color and B-mode data into a single image frame based on predetermined write priority rules, and applying selected color maps (e.g. red, green, blue values) to represent the flow signal parameter (e.g., mean velocity) in color, and selected gray maps to represent the B-mode background echo data.

Figure 8:
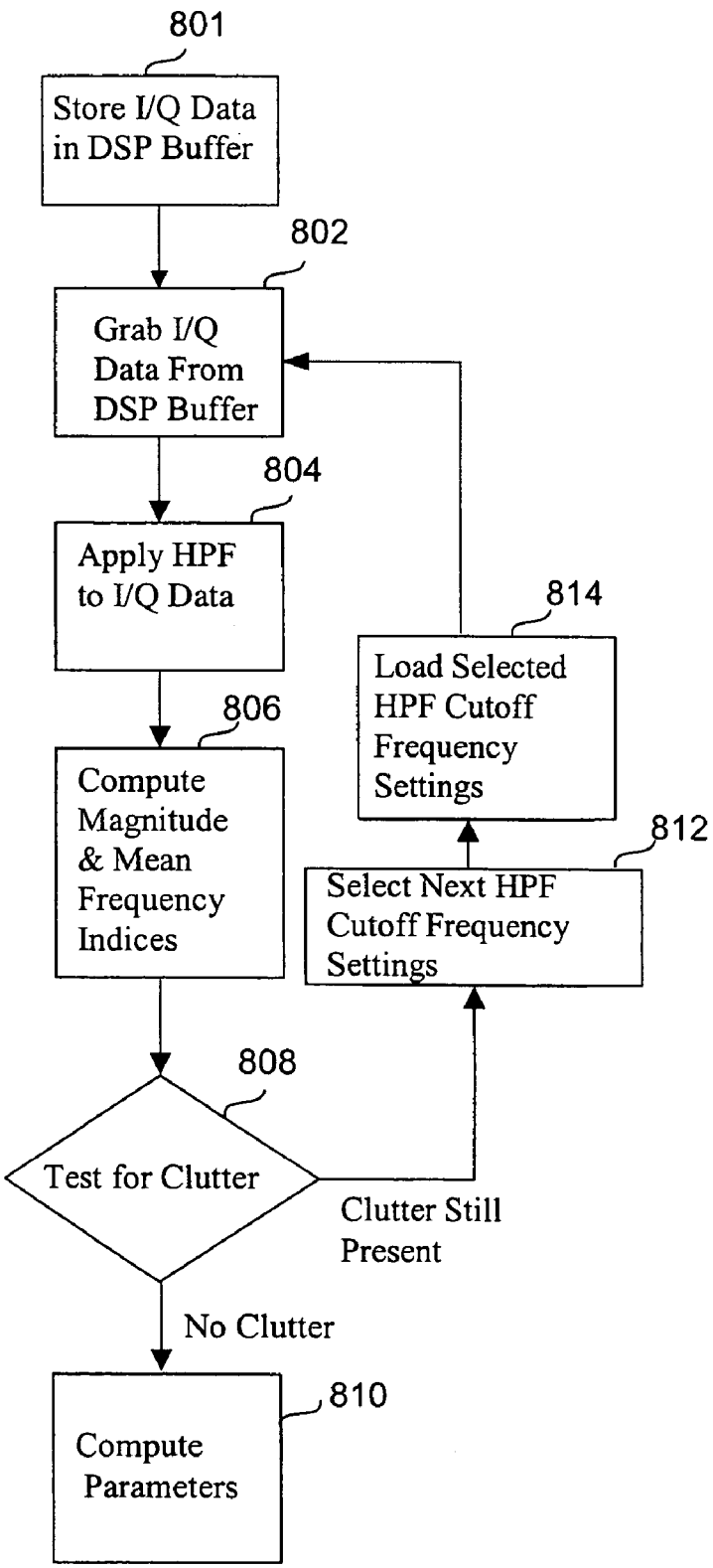
FIG. 8 is a flowchart for an adaptive clutter filtering method according to one embodiment of the invention of FIG. 7B.

FIG. 8 is a flowchart for an adaptive clutter filtering method 800 according to an embodiment of the invention. Although image processor 734 is included in the embodiment of FIG. 7A, method 800 may be implemented as hardware, software, and/or firmware within the color flow processor of any ultrasound system that processes the I/Q data 744 (from I/Q signals 726) from all spatial locations within a user specified ROI in the line, plane, or volume of insonation, regardless of which transmit and receive system and focusing processes are used to acquire I/Q signals 726.

In step 801, labeled "Store I/Q Data in DSP Buffer," takes I/Q data 744 from memory buffer 732 and stores I/Q data 744 in a DSP buffer. Memory buffer 732 may store many frames of I/Q data, while the DSP buffer stores a smaller amount of I/Q data such as a single frame or a portion of a frame. In step 802, labeled "Grab I/Q Data From DSP Buffer," one or more packets of I/Q data 744 that correspond to one or more acoustic points within the color ROI, are read from memory buffer 732. In step 804, labeled "Apply HPF to I/Q Data," the I/Q data 744 is passed through an HPF loaded with a pre-selected set of filter coefficients. The sets of HPF coefficients for a range of $N_f$ cutoff frequency settings (or parameters) is predetermined and stored in memory buffer 732 for each color flow imaging setup, which may include, but is not limited to, probe type, transmit frequency, application type, packet size and PRF. The HPF may be implemented using standard FIR or IIR filters. The HPF coefficients may range from a simple FIR filter [1,−1] to higher order filters involving 10 or more real and/or complex coefficients. For the purpose of this disclosure, the term "cutoff frequency setting" of an HPF is used to characterize its clutter rejection power at different frequencies. That is, a higher cutoff setting may entail more than just choosing a filter with a higher stopband cutoff frequency at, for example, the −50 dB level, but also changing the filter order, sharpness, and/or shape of the HPF transition band. The HPF cutoff frequency settings may be adjusted by changing which HPF coefficients are used and/or the values of the HPF coefficients and/or any other parameters associated with the HPF. As examples of other parameters, the filtering operation can conceivably be implemented in the frequency domain by multiplying the FFT of the signal with a filter function, and then converting the result back to the time domain. In that implementation, the filter parameters may specify a characteristic function (e.g., Butterworth, Chebychev) that represents the frequency response of the filter. The characteristic function may have parameters other than frequency as inputs, such as the number of terms. The ordering of the filters may depend upon the type of clutter expected. Basically, the lowest cutoff setting should be used in absence of clutter, while the highest cutoff setting is designed to eliminate the highest possible clutter frequencies associated with tissue motion.

In an embodiment, the HPF cutoff frequency setting is automatically adjusted for each I/Q data packet on a packet by packet basis (i.e., one packet per acoustic point). An iterative search algorithm may be performed to find the optimal HPF cutoff frequency that is just high enough to remove all the clutter.

In step 806, labeled "Compute Magnitude and Mean Frequency Indices," some indices of the magnitude and mean frequency of filtered I/Q data are computed. The quantities computed during step 806 are for the purpose of carrying out step 808. In step 808, labeled "Test for Clutter," tests are performed using the quantities computed in step 806 to test for the presence of clutter. A criterion for determining and/or detecting the presence of clutter is when the magnitude of the filtered I/Q data is greater than a certain threshold and/or whether the absolute value of the mean frequency shift (the average phase change per PR1) is lower than a certain clutter frequency threshold. Mathematically these clutter presence criteria can be written as Magnitude>clutter magnitude threshold?

and/or

|Mean phase change/PR1|<clutter frequency threshold?

There are many measures that can be used to quantify the signal magnitude and mean frequency/phase change to detect the presence of clutter. For example, the magnitude may be represented by the total signal energy, E, which is given by $$E=\Sigma[I^2(n)+Q^2(n)],$$

or by $$\Sigma[|I(n)|+|Q(n)|],$$

where n=1, 2, 3, . . . , is the time index, and the summation is over all n within the packet. The total signal energy E is equivalent to the zero order autocorrelation (R0) of the filtered signal. A rough estimate of the mean frequency can be obtained using a zero-crossing counter (i.e., measuring the frequency by counting of the number of times the signal crosses the zero line over a known time period), while an accurate but inefficient method of calculating the mean frequency is to compute the centroid (see, for example, U.S. Pat. No. 5,349524, cited above) of the FFT of the data samples, for example. In the preferred embodiment, the first order autocorrelation function of the filtered data is calculated by $$R1 = \sum_{n=2}^{N} [I(n-1) + jQ(n-1)] * [I(n) - jQ(n)].$$

where the summation is over all n time indices within a packet, and N is the number of flow samples per packet. From R1 the mean phase change <Δθ> per PRI can be computed as $$<\Delta\theta>=(1/\pi)ang(R1),$$

where ang(.) denotes the phase angle of a complex quantity. Note that evaluation of ang(R1) involves forming the ratio of its imaginary to real part, and an arc tangent operation, both relatively expensive for real-time implementation.

However, at this stage in the algorithm, it is not necessary to obtain precise estimates of the magnitude and mean phase/frequency change. Rather, it suffices to know whether these are larger or smaller than predefined thresholds. Hence, in one embodiment, the criterion that the absolute value of the mean frequency change $|<f>|=|<\Delta\theta>|/\text{PRI}$ is less than some clutter frequency threshold $f_{Th}$, is equivalent to asking if the following is true:

$$|<\Delta\theta>|=(1/\pi)|\text{ang}(R1)|<f_{Th}/\text{PRF}$$

which can be re-written as $$|\text{ang}(R1)|<\pi(f_{Th}/\text{PRF}).$$

An alternative criterion for determining and/or detecting the presence of clutter is to compare a composite index that is some function of both the magnitude and mean frequency of the filtered signal, against a single threshold.

Figure 9:
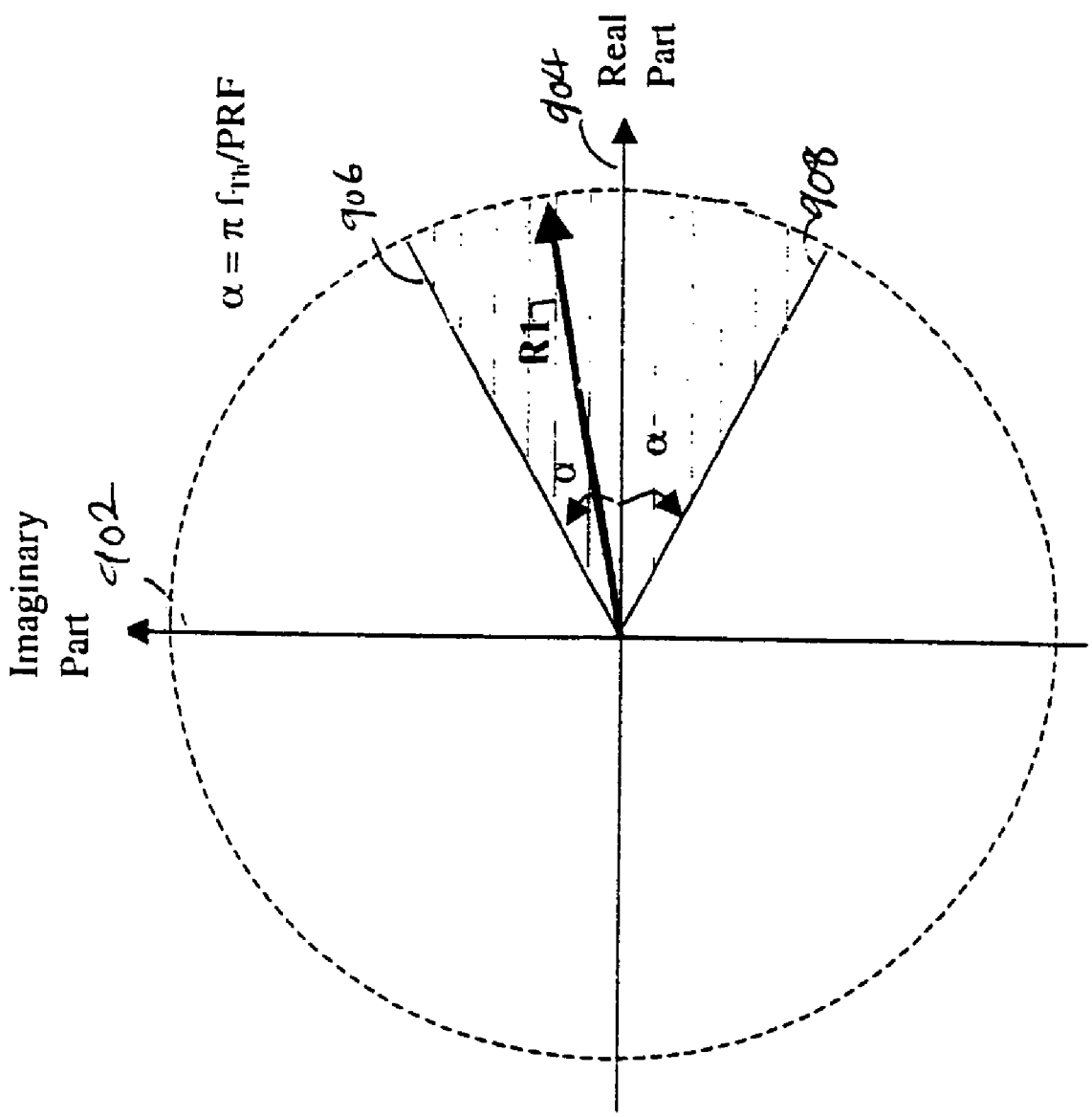
FIG. 9 is a plot of the first order autocorrelation estimate in the complex plane, and the bounds on its phase angle in the clutter frequency threshold test.

FIG. 9 is a plot 900 of the first order autocorrelation R1 estimated in the complex plane having vertical axis 902 and horizontal axis 904, and the bounds 906 and 908 on its phase angle in the clutter frequency threshold test of step 808 of FIG. 8. R1 is viewed as a vector in the complex plane where the vertical axis 902 represents the imaginary axis, and the horizontal axis represents the real axis. In practice, the smallest PRF setting available to the user is at least 2 times larger than the clutter frequency; hence, it is reasonable to assume that $f_{Th}/\text{PRF}<\frac{1}{2}$. This means that the above angle test is equivalent to asking if R1 falls within a sector bounded by $+/-\alpha$, where $\alpha=\pi(f_{Th}/\text{PRF})<\pi/2$; i.e., $\alpha$ is within the right half-plane.

Since $\text{ang}(R1)=\tan^{-1}(y/x)$ in the right half-plane (where x and y denote the real and imaginary parts of R1, respectively) the mean phase/frequency criterion for determining the presence of clutter is equivalent to $$|y|<x*C,$$

in which $C=\tan(\pi t_{Th}/\text{PRF})$ is a positive-valued constant that can be predetermined as a function of PRF.

To summarize, the clutter in the filtered I/Q data packet can be detected by testing if Magnitude index>clutter magnitude threshold and if $$|y|<x*C.$$

In general, the magnitude and clutter frequency thresholds are both dependent on iteration number. For example, as the cutoff frequency setting increases, the frequency threshold for clutter would also likely need to be adjusted.

Referring again to FIG. 8, step 808 includes exit conditions, which if met continues method 800 to step 810, which will be discussed below. The exit conditions may include a determination that no clutter is present or that all available HPF cutoff frequency settings have been selected, tested, and determined to be inadequate for removing the clutter. If the exit conditions are not met and there still remain HPF cutoff frequency settings that have not been selected and tested, method 800 proceeds to step 812, labeled "Select Next HPF Cutoff Frequency Settings" in which the next cutoff frequency setting is selected depending on which cutoff frequency settings have been tested. Step 812 produces inputs that affect step 814, labeled, "Load Selected HPF Cutoff Frequency Settings." In step 814 the selected HPF cutoff frequency setting (e.g., FIR filter coefficients) is loaded into the HPF of step 804. Depending on the processing power available and on the frame rate requirements, a suitable number ($N_f$) of HPF cutoff frequency setting selections will be available for selection in the iterative scheme. The order in which HPF cutoff frequency settings are selected is based on how much clutter they reject. For example, if there are only two HPF cutoff frequency settings to choose from ($N_f=2$), the initially selected HPF cutoff frequency setting is the one having the low frequency cutoff setting, and if after filtering with the initially chosen HPF cutoff frequency setting the clutter is still present, the higher cutoff frequency setting is applied.

For $N_f>2$, at least two search strategies or preferred embodiments are possible including a sequential search (starting with an extreme cutoff frequency setting) and a binary search (starting with the middle cutoff frequency setting of the predetermined range). The advantage of the sequential search is that the minimum number of iterations is one. In other words, no further iterations are necessary if the filtered signal is deemed free of clutter after the first pass. Whereas, with a binary search, at least two iterations are needed for each data packet. However, if $N_f$ is large, a binary search tends to converge faster onto the optimal HPF cutoff frequency setting than a sequential search.

For a binary search, an HPF cutoff frequency setting in the middle of the cutoff frequency range is first applied to I/Q signals 744. In a binary search, if the clutter threshold test for the first iteration is negative (i.e., magnitude not too large and mean frequency not too low), then the magnitude and R1 estimates are stored in memory buffer 732 or another part of memory system 406 and the next lower cutoff frequency setting is chosen to re-process I/Q signals 744, and the above threshold tests are repeated until an exit condition occurs. An exit condition in a binary search is finding two consecutively ordered filters, one with a positive result for the threshold test and one with a negative result for the threshold test. An exit condition in a sequential search may be when either a status change occurs (e.g., the clutter test becomes positive), in which case the cutoff frequency setting of the previous iteration must be optimal, and the corresponding stored magnitude and R1 values are used or when no status changes (i.e., the clutter test remains negative) even when the lowest cutoff frequency setting is reached, in which case the lowest setting will be used. In an alternative embodiment of a sequential search the status change may be that the clutter test becomes negative, in which case the cutoff frequency setting of the present iteration is selected.

If, on the other hand, the clutter threshold tests for the first iteration prove positive (i.e., significant clutter is still present), then the original I/Q data packet is reprocessed at a higher cutoff frequency setting, and the above steps are repeated until one of the two exit conditions as described above is true.

In practice, only a small number of iterations may be needed before reaching the point of diminishing returns. It is expected that for many applications even $N_f=2$ may suffice. Compared to prior adaptive wall filter methods that always perform mean frequency estimation twice for each acoustic point, the present algorithm that chooses between a "high" and a "low" cutoff frequency setting ($N_f=2$) should be more computationally efficient in at least two ways. First, if the initial (low) filter cutoff frequency setting is chosen properly, an additional iteration (high cutoff frequency setting) is needed only if tissue motion is detected (which occurs over only a fraction of the cardiac or breathing cycle, and in a portion of the image pixels). Second, the angle estimate, which requires a division and an arctangent operation, needs only be computed once. Specifically, the arc tangent only needs to be calculated in step 810 after the second or final iteration.

In general, the number of iterations can vary from acoustic point to acoustic point for each image frame. A higher level of processing control based on some global criteria may be used to maintain a more consistent or predictable processing time per image frame. Many different global criteria are possible. For example, one global criterion could be if tissue motion (that prompts the use of higher filter cutoff frequency settings) is detected in a predefined percentage of the acoustic points (e.g., 40%) within the user-selected color flow ROI, then the next higher filter cutoff frequency setting may be set as the default filter in an attempt to speed up (one less iteration) the processing of the remaining pixels, at the expense of potentially missing a portion of the lowest flow components in some of the remaining pixels (which should not be a serious sacrifice). A second global criterion could be if a full-size ROI is selected by the user, then the larger number of iterations N is allowed only for a central area within the ROI. These two global criteria could be used separately or in combination. The use of a higher number of iterations in the central area assumes the user is mainly interested in the flow in that central area, but the higher number of iterations could be applied to other parts of the ROI instead, depending on the interests of the user. The user may be given the option of choosing the region within the ROI that allows for more than one iteration. In the extreme case, no iterations may be allowed outside the central area, or another area chosen by the user, of the ROI.

No matter the search method, upon meeting the exit conditions method 800 proceeds to step 810 labeled "Compute Flow Parameters," in which flow parameters are computed to a precision adequate for the color encoded display. The flow parameters refer to the mean Doppler frequency/velocity, and/or total Doppler power, and other standard flow related parameters including velocity variance, as required by the user selected color flow imaging mode. In the velocity imaging mode, the mean velocity is color coded for image display. In the power Doppler imaging mode, the total power is color coded for display. Depending on which parameters are used for testing the magnitude and mean frequency in the adaptive algorithm, some of the results such as total energy or power (R0) and autocorrelation estimates (R1) for the optimal HPF setting can be used directly or in part for the computations of the needed flow parameters.

Although in the above description the clutter was derived from stationary and/or relatively slow moving tissues and the flow under investigation was relatively fast moving, such as blood, the same method can be applied in situations in which the clutter is the relatively fast moving fluid flow and the flow under investigation are stationary and/or relatively slow moving objects, except a low pass filter would be used rather than a HPF. Also, the same method might be used to select an optimal band pass or notch filter if there is high frequency and low frequency clutter. In another embodiment both the clutter information and the information of the rest of the frequency spectrum may be of interest. Consequently, rather than discarding the clutter information, it is extracted and analyzed and/or processed with or without the rest of the spectrum. For example, when the motion under investigation is the movement of a tissue wall, such as the heart, the high frequency flow spectrum of the blood is the clutter.

Although the invention has been described with reference to specific embodiments, it will be understood by those skilled in the art that various changes may be made and equivalents may be substituted for elements thereof without departing from the true spirit and scope of the invention. In addition, modifications may be made without departing from the essential teachings of the invention.

What is claimed is:

1. An ultrasound clutter filter system, comprising:
    a processor configured to iteratively select an optimal high pass filter for progressive, ordered filtering of clutter from ultrasound color flow imaging data wherein a determination of whether a high pass filter is optimal is made by comparing an index to a threshold for that index, the index being computed using a mathematical formula including a mean frequency and a magnitude of a filtered signal, wherein a high pass filter input for each iterative selection is the original ultrasound color flow imaging data.

2. The system of claim 1 wherein the processor is configured for selecting said optimal high pass filter for performing filtering over each packet of flow data that corresponds to an acoustic point in a color flow region of interest.

3. The system of claim 1 wherein the processor is configured to select the optimal high pass filter is if the filtered signal is less than a threshold.

4. The system of claim 1 wherein the processor is configured to select the optimal high pass filter is if a magnitude of a portion of the filtered signal that is within a predetermined frequency range is less than a threshold.

5. The system of claim 1 wherein the processor is configured to select the optimal high pass filter is if a total energy of the filtered signal is less than an energy threshold.

6. The system of claim 1 wherein the processor is configured for selecting said optimal high pass filter for performing filtering in real time while imaging.

7. The system of claim 1 further comprising a finite number of high pass filters from which the optimal high pass filter is selected.

8. The system of claim 7 in which the finite number of high pass filters is two.

9. The system of claim 7, wherein the finite number of high pass filters comprises a finite impulse response filter.

10. The system of claim 7, wherein the finite number of high pass filters comprises an infinite impulse response filter.

11. An ultrasound clutter filter system, comprising:
    a processor configured to iteratively select an optimal high pass filter for progressive, ordered filtering of clutter from ultrasound color flow imaging data wherein a criterion for selecting the optimal high pass filter is if a mean frequency of filtered signal data is less than a clutter frequency threshold wherein if the mean frequency is less than the clutter frequency threshold is determined by whether an absolute value of an imaginary part of a first order autocorrelation of the filtered signal data is less than a constant times a real part of the autocorrelation, where the constant is determined by the clutter frequency threshold, wherein a high pass filter input for each iterative selection is the original ultrasound color flow imaging data.

12. The system of claim 11 wherein the processor is further configured to select the optimal high pass filter further comprises if the filtered signal data is less than a threshold.

13. The system of claim 11 wherein the processor is further configured to select the optimal high pass filter further comprises if a magnitude of a portion of the filtered signal that is within a predetermined frequency range is less than a threshold.

14. The system of claim 11 wherein the processor is further configured to select the optimal high pass filter further comprises if a total energy of the filtered signal is less than an energy threshold.

15. The system of claim 11 wherein the filtering high pass filter is configured to perform over each packet of flow data that corresponds to an acoustic point in a color flow region of interest.

16. The system of claim 11 wherein the filtering high pass filter is configured to perform in real time while imaging.

17. The system of claim 11 further comprising a finite number of high pass filters from which the optimal high pass filter is selected.

18. The system of claim 17 in which the finite number of high pass filters is two.

19. An ultrasound clutter filtering method, comprising:
iteratively selecting an optimal high pass filter for progressive, ordered filtering wherein the iteratively selecting comprises computing an index using a mathematical formula including a mean frequency and a magnitude of a filtered signal and determining whether a filter is optimal by comparing the index to a threshold, wherein a high pass filter input for each iterative selection is original ultrasound color flow data; and
filtering clutter from the ultrasound color flow data until the clutter is substantially removed.

20. The method of claim 19 wherein the filtering comprises filtering an individual packet of the ultrasound color flow data that corresponds to an acoustic point in a region of interest.

21. The method of claim 19 wherein the filtering is performed in real time while collecting the ultrasound color flow data.

22. The method of claim 19 wherein the iteratively selecting further comprises determining if the filtered signal is less than a threshold.

23. The method of claim 19 wherein the iteratively selecting further comprises determining if a magnitude of the filtered signal is less than a than a frequency threshold.

24. The method of claim 19 wherein the iteratively selecting further comprises selecting a high pass filter from a finite number of high pass filters.

25. The method of claim 19 wherein the iteratively selecting further comprises selecting one of two high pass filters.

26. The method of claim 25, wherein one of the two high pass filters comprises a finite impulse response filter.

27. The method of claim 25, wherein one of the two high pass filters comprises an infinite impulse response filter.

28. The method of claim 19 wherein the iteratively selecting further comprises determining if a magnitude of a color flow signal in a preselected frequency range is less than a color flow signal threshold wherein a phase shift is less than a phase shift threshold.

29. An ultrasound clutter filtering method, comprising:
iteratively selecting an optimal high pass filter for progressive, ordered filtering of ultrasound color flow data wherein the iteratively selecting comprises determining if a magnitude of a color flow signal in a preselected frequency range is less than a color flow signal threshold, wherein the determining includes determining whether an absolute value of an imaginary part of a first order autocorrelation of the color flow data is less than a constant times a real part of the autocorrelation, where the constant is determined by a frequency threshold, wherein a high pass filter input for each iterative selection is the original ultrasound color flow data, and;
filtering clutter from the ultrasound color flow data until the clutter is substantially removed.

30. The method of claim 29 wherein the filtering comprises filtering an individual packet of the ultrasound color flow data that corresponds to an acoustic point in a region of interest.

31. The method of claim 29 wherein the filtering is performed in real time while collecting the ultrasound color flow data.

32. The method of claim 29 wherein the iteratively selecting further comprises determining if the filtered signal is less than a threshold.

33. The method of claim 29 wherein the iteratively selecting further comprises determining if a magnitude of frequency of the filtered signal is less than a frequency threshold.

34. The method of claim 29 wherein determining further comprises determining whether a phase shift is less than a phase shift threshold.

35. The method of claim 29 wherein the iteratively selecting further comprises selecting a high pass filter from a finite number of high pass filters.

36. The method of claim 29 wherein the iteratively selecting further comprises selecting one of two high pass filters.

* * * * *